United States Patent [19]

Pusztaszeri

[11] 4,014,900
[45] Mar. 29, 1977

[54] PURIFICATION OF 2-PYRROLIDONE

[76] Inventor: Stephen F. Pusztaszeri, P.O. Box 1181, Port Chester, N.Y. 10573

[22] Filed: June 24, 1974

[21] Appl. No.: 482,166

Related U.S. Application Data

[63] Continuation-in-part of Ser. No. 224,274, Feb. 7, 1972, abandoned.

[52] U.S. Cl. .................................. 260/326.5 FN
[51] Int. Cl.$^2$ .................................. C07D 207/26
[58] Field of Search ......... 260/326.5 FN, 326.5 FM

[56] References Cited

UNITED STATES PATENTS

| | | | |
|---|---|---|---|
| 2,806,856 | 9/1957 | Robinson | 260/326.5 |
| 2,828,307 | 3/1958 | Soeterbroek et al. | 260/326.5 |
| 2,939,869 | 6/1960 | Carlson | 260/326.5 FN |
| 2,964,535 | 12/1960 | Clements | 260/326.5 |
| 3,006,817 | 10/1961 | Ney | 260/326.5 |
| 3,290,329 | 12/1966 | Doerfel | 260/326.5 FM |

FOREIGN PATENTS OR APPLICATIONS 37-16038  10/1962  Japan ........................ 260/326.5

*Primary Examiner*—Frederick E. Waddell
*Attorney, Agent, or Firm*—Haseltine, Lake & Waters

[57] ABSTRACT

Commercially efficient process for purifying commercial 2-pyrrolidone into substantially pure anhydrous 2-pyrrolidone comprises treating liquid impure 2-pyrrolidone with a minor amount of a solid substantially anhydrous metal hydroxide and flash vaporizing from a heated surface under closely controlled temperature and pressure conditions in a molecular distillation apparatus, without establishing a vapor pressure equilibrium. Very dark colored commercial 2-pyrrolidone may be given a preliminary purification treatment by cooling until the 2-pyrrolidone solidifies and draining off the dark-colored liquid containing impurities.

10 Claims, No Drawings

PURIFICATION OF 2-PYRROLIDONE

CROSS-REFERENCE TO RELATED APPLICATION

This application is a continuation-in-part application of Ser. No. 224,274, filed February 7, 1972, now abandoned.

BACKGROUND OF THE INVENTION

Commercial grade 2-pyrrolidone generally contains about 1 to 2% or more by weight of certain impurities such as water, butyrolactone, 2-butyne-1,4-diol, 2-butene-1,4-diol, 1,4-butanediol, bipolar mesomer, amino acids and other unknown materials, depending upon the method by which the material was made and handled, and which do not present a problem from some end uses to which the material is applied but which render the material unsuitable for other end uses.

Several purification processes have been proposed over the years, including treatment with hydrides, hydroxides, pentoxides, acid anhydrides, various volatile solvents, and the like. However such known processes have a variety of deficiencies including a lack of efficiency resulting from a high amount of waste of the commercial grade 2-pyrrolidone. Also some of these processes are only effective with respect to 2-pyrrolidone produced according to a certain method while other proposed processes result in the production of 2-pyrrolidone which is not truly pure as evidenced by its inability to form a high viscosity homopolymer or to undergo polymerization at all and by its inability to maintain a stable clear color for more than a month or so.

SUMMARY OF THE INVENTION

It is the principal object of the present invention to provide a method for converting commercial grade 2-pyrrolidone into substantially pure, substantially anhydrous 2-pyrrolidone, thus providing a commercial method of great efficiency.

It is another object of this invention to provide an efficient method for purifying coemmercial grade 2-pyrrolidone, which method is effective regardless of the method by which the 2-pyrrolidone was produced.

It is still another object of this invention to provide an efficient method for producing substantially pure anhydrous 2-pyrrolidone which is capable of being polymerized in a high yield to form a high viscosity fiber-forming homopolymer.

These and other objects and advantages of the present invention will be apparent to those skilled in the art in the light of the present disclosure.

The present invention consists essentially of treating a solution of a small amount, of a solid hydroxide of an alkali metal of alkaline earth metal in liquefied impure 2-pyrrolidone in a molecular distillation apparatus under carefully controlled temperature and pressure conditions. The molecular distillation apparatus must be of such a design that a thin film of the metal hydroxide/2-pyrrolidone solution is applied to a heated surface under reduced pressure to flash vaporize the 2-pyrrolidone without forming a vapor-liquid equilibrium, so that substantially all of the evaporating 2-pyrrolidone molecules move directly from the heated surface to a cooled surface where they are condensed and subsequently collected. Since there is no vapor pressure equilibrium formed, substantially none of the vaporized 2-pyrrolidone molecules return to the distilland. This is important because 2-pyrrolidone is a heat-sensitive material and prolonged heating leads to the formation of decomposition products and loss of yield. The metal hydroxide combined with the impurities is non-volatile and is continuously drained off during the process. Water is removed in a vacuum trap.

DESCRIPTION OF PREFERRED EMBODIMENTS

The first step of the invention involves liquefying 2-pyrrolidone, such as by raising the temperature thereof above its melting point and no higher than about 28° C., preferably between about 25° and 27° C to insure total melting, and dissolving therein a dry, i.e., solid alkali metal hydroxide or alkaline earth metal hydroxide which is considered to be substantially anhydrous within the context of the present invention. The minimum amount of metal hydroxide is critical to the present process, since insufficient hydroxide will not tie down the impurities. An excess of hydroxide is uneconomical, since it will form a salt with 2-pyrrolidone, thus reducing the yield of purified 2-pyrrolidone. For the generally available commercial grade of 2-pyrrolidone, it has been found that an amount of from about 0.1 to 0.8% preferably 0.1 to 0.5% by weight based upon the weight of the liquefied 2-pyrrolidone, meets these requirements.

The second step of the present process involves slowly introducing the 2-pyrrolidone-metal hydroxide solution to a molecular still which is a specialized type of vacuum distillation apparatus. Preferably the solution is initially degassed and then it is fed slowly onto the heated surface of the molecular still. The temperature of the heated surface and the pressure within the still will depend upon the type of vacuum distillation apparatus. Generally, the lower the pressure, the lower the temperature of the heated surface required to flash vaporize the 2-pyrrolidone without forming a vapor pressure equilibrium. It is conceivable that a pressure as high as 20 mm Hg could be employed. The optimum temperature and pressure conditions in any type of apparatus are chosen so as to give the maximum rate of distillation, e.g., 90°–120° C at about 0–5 mm Hg. Vacuum pressures of 0.1 mm Hg and less are preferred. The rate at which the solution is fed into the molecular still preferably should be adjusted so that some small amount of 2-pyrollidone is allowed to pass the entire length of the heated, surface, e.g., column or wall, and drain into the impurities flask. Otherwise the impurities and the metal hydroxide will solidify on the heated surface and interfere with the smooth operation of the still. The lost 2-pyrrolidone functions as a solvent for the impurities and for the metal hydroxide and represents only about 2 to 6% of the total content.

Water present in the starting solution is removed from the molecular still as vapor by means of the vacuum line. Water is so volatile under the temperature and pressure conditions within the still that the temperature of the condensation surface e.g. wall or column is well in excess of the vaporization temperature of the water.

The solution introduced onto the heated surface of the molecular still comprises the metal hydroxide dissolved in the impure 2-pyrrolidone, and the metal hydroxide which has combined with the impurities to produce materials which are non-volatile under these conditions. These non-volatile materials, together with a small amount of liquid 2-pyrrolidone, drain down the heated surface and are collected in the flask associated therewith. The bulk of the pure 2-pyrrolidone flash-vaporizes from the heated surface and condenses on the condensation surface of the apparatus due to the fact that the temperature of the condensation surface is maintained well below the minimum vaporization temperature of the pure 2-pyrrolidone under the minimum reduced pressure within the system. The condensed pure anhydrous 2-pyrrolidone drains down the condensation surface and is collected in the flask associated therewith.

The weight of the impurities plus the hydroxide and the lost 2-pyrrolidone collected in the flask associated with the heated column represents from 5 to 10% of the weight of the starting material. Under optimum conditions, the pure anhydrous liquid 2-pyrrolidone collected in the flask associated with the condensation surface is clear, odorless and colorless, has a density at 25° C. of 1.117, a melting point of 24.8° C., a refractive index at 30° C. of 1.484, a pH of 10.2 in 10% aqueous solution, and is stable and resistant to discoloration after over six months' exposure to light.

The use of a molecular vacuum distillation apparatus providing a very short contact time on the heated surface is essential to the present process, since prolonged heating of 2-pyrrolidone in the presence of alkali or acid, and even trace amounts of water can result in hydrolysis, rupture of the pyrrolidone ring anf formation of amino acids and/or amino acid salts. In the molecular still the heated element has a surface temperature equal to or slightly above the vaporization temperature of the 2-pyrrolidone unde the reduced pressure of the system, so that the bulk of the 2-pyrrolidone is flash-vaporized upon contact with the heated surface. Thus the duration of heating the 2-pyrrolidone in the presence of the alkali and any water present in the system is limited to at most a few seconds.

Several types of commercially available molecular distillation apparatus are described in Perry's "Chemical Engineering Handbook," 3rd. Edition, Page 655 ff and 4th Edition Pages 17–29 to 17–33. Those which employ a heated tray or pot to contain any substantial depth of the distilland would not be suitable for the process of the present invention, since unnecessary prolonged heating of the 2-pyrrolidone is undesirable.

A common type of molecular still used in laboratory or pilot plant operations is the falling film molecular still. This type was used in the examples of the present application. One structural embodiment of a falling film still comprises a center heated column and an outer condensation wall closely spaced therefrom and the vacuum is maintained in the space therebetween. The heated column is associated with a flask which receives the liquid which passes down the length of the surface of the column without evaporating therefrom, i.e., the non-volatiles, while the outer condensation wall is associated with a separate flask which receives the liquid which evaporates from the surface of the center column and condenses on the inner surface of the outer wall.

Another type of falling film molecular still employs a cooled central condensation column and a heated outer wall or jacket with a vacuum therebetween. The solution to be purified is slowly fed to the inner surface of the heated wall and the 2-pyrrolidone is flash-vaporized and condenses on the surface of the central condensation column. The condensed 2-pyrrolidone drains to a flask associated with the surface of the column, generally with the assistance of blades which continuously wipe the condensed 2-pyrrolidone from the surface of the column and cause it to drain into the flask more quickly. The mon-volatile impurities remain on the surface of the heated outer wall and drain into a separate flask associated therewith.

In determining suitable temperature and pressure conditions to be used in any given molecular distillation apparatus, use is made of the following equation based on the Langmuir-Knudsen interpretation of the Maxwell-Boltzmann law:

$$N = PA \sqrt{\frac{1}{2\pi MRT}}$$

where
$N$ = Number of molecules leaving evaporator per second
$P$ = Vapor pressure (dynes/cm$^2$)
$A$ = Area of distilling surface
$m$ = Molecular Weight
$R$ = Gas Constant 8.3 × 10$^7$ ergs per °K/mol
$T$ = Temperature °Kelvin (°K)
The above can be reduced to:

$$W = 0.429 \, p \sqrt{\frac{M}{T}}$$

$W$ = Weight of vapor leaving evaporator (1bs/hr/ft$^2$ of evaporator surface area)
$p$ = Pressure in microns Hg
$M$ = Molecular weight
$T$ = Temperature (°K)

Molecular stills of the falling film type are commercially available, such as from Kontes Glass Company, Vineland, N.J., under the designation Falling Film Molecular Still No. K 285600 (heated central column type) and from Arthur F. Smith, Inc., Rochester, New York, under the designation Rota Film Molecular Still (heated outer wall type). In the Rota Film type; a rotating wiper insures even spreading of the film on the heated surface causing rapid molecular movement.

The metal hydroxides suitable for use according to the present invention are the alkali metal hydroxides such as sodium hydroxide, potassium hydroxide and lithium hydroxide and the alkaline earth metal hydroxides such as barium hydroxide and calcium hydroxide. The most preferred materials are potassium hydroxide and sodium hydroxide, in that order. The metal hydroxide must be used in substantially dry, i,e., solid, condition and in no case should it contain more water than is present in the commercially available "analytical grade" of the particular metal hydroxide used. For instance, analytical grade potassium hydroxide contains 10–13% water, analytical grade sodium hydroxide contains 1–3% water, analytical grade lithium hydroxide contains 1% water and analytical grade barium hydroxide contains 10–11% water. These materials ? ɔ substantially anhydrous within the context of the present invention. The presence of small amounts of water in the analytical grade materials renders these materials more soluble in the 2-pyrrolidone than if they were absolutely anhydrous. The presence of large amounts of water results in the production of substantia!

amounts of amino acids such as 4-aminobutyric acid with resultant loss of substantial amounts of 2-pyrrolidone and decreased efficiency of the purification process. This same result can occur when an excess amount of water is added to the 2-pyrrolidone-metal hydroxide solution and the solution is subjected to prolonged heating such as in conventional reflux ratio distillation.

Flash-vaporization occurs when a liquid is slowly applied to a heated surface having a temperature equal to or greater than the vaporization temperature of the liquid at the pressure of the system. The duration of heating of the liquid is small since it is vaporized quickly. The vaporized material can then be condensed on an adjacent surface having a temperature below the vaporization temperature of the material at the pressure of the system. If the distance of transfer is comparable with the mean free path of the vapor molecules, the process is known as "molecular distillation." Otherwise a somewhat greater distance of transfer is utilized in what is known as "unobstructed path distillation." Both types may be used in the present invention.

The following examples are set forth as an illustration of the process of the present invention and should not be considered limitative.

EXAMPLE 1

Commercial grade 2-pyrrolidone commercially available from General Aniline & Film Corporation or from B.A.S.F. Corporation is chilled in its shipping container to a temperature of about 23° to 24° C. to cause the 2-pyrrolidone to completely crystallize, i.e. solidify in a dark brown mother liquor. The mother liquor is poured off from the solid crystals and amounts to 1 to 2% by weight of the initial material.

The solid material is warmed to 25° to 27° C to cause it to liquefy totally and 110 grams are drawn off and 0.6 gram of analytical grade potassium hydroxide is dissolved therein.

The solution is then placed into the funnel of a falling film molecular still and is degassed for 10 minutes. The still has a central column which is heated internally by vapors of toluene to a constant temperature of 110.6° C. The space between the central heated column and the outer condensation wall or jacket is maintained at a vacuum pressure of 0.5 mm. mercury pressure. The degassed solution is allowed to enter the still dropwise upon the surface of the heated column where the volatile 2-pyrrolidone is vaporized while the non-volatile impurities remain in liquid condition on the heated column together with a small amount of 2-pyrrolidone which functions as a solvent. The small amount of water which is present in the solution is also vaporized and the water vapor, being more volatile that the 2 -pyrrolidone vapor, cannot condense and is removed through the vacuum line and trapped outside the still. The 2-pyrrolidone vapors condense on the inner surface of the condensation wall or jacket which has a temperature of about 50° C due to the fact that the outer surface of the jacket is exposed to room temperature of about 27° C. If desired, the jacket can be cooled by cold water.

The non-volatile impurities drain and are collected in the flask associated with the surface of the heated column and amount to 10 parts by weight of the initial solution. The condensed 2-pyrrolidone drains from the condensation wall and is collected in the flask associated therewith and amounts to 100 parts by weight of the initial solution. The 2-pyrrolidone is odorless and colorless and remains odorless and colorless after exposure to light for six months. It has a pH of 10.2 in 10% aqueous solution, a refractive index at 30° C of 1.484, a density at 25° C of 1.117, a melting point of 24.8° C and a boiling point of 248° C. at 760 mm.

EXAMPLE 2

5.5 grams of analytical grade potassium hydroxide is dissolved in 1100 grams of liquefied commercial 2-pyrrolidone and the solution is added to the funnel container of a 4 inch Asco Molecular Still Apparatus (heated wall type). The solution is degassed for 10 minutes and then slowly introduced against the heated wall of the still which is electrically heated to a temperature of from 110° C to 115° C at a vacuum pressure of from $10^{-4}$ to 2 mm. pressure. The bulk of the 2-pyrrolidone flash-vaporizes from the heated wall and condenses on the cool surface of the center condensation column which is cooled internally by means of cold water. Spiral rotor blades wipe the liquid impurities from the heated wall and thus cause them to drain more quickly into a flask associated with the heated wall. The impurities, together with a small amount of liquid 2-pyrrolidone to keep the impurities and the hydroxide in solution, drain down the heated wall with the assistance of the spiral rotor bladesand are collected in a separate flask associated therewith. The pure liquid 2-pyrrolidone drains down the condensation surface into the flask associated therewith. The recovered pure 2-pyrrolidone amounts to 979 grams and the impurities plus the hydroxide and lost 2-pyrrolidone amount to about 126 grams. The product has the same properties as in Example 1.

The optional preliminary solidification step illustrated in Example 1 is generally used only in cases where the starting material has a color, indicating the presence of substantial amounts of the bipolar mesomer or other impurities. The darker the color the more advantageous it is to employ the initial solidification step to separate out the colored mother liquor.

The present process is a substantially anhydrous purification process in which no water is added except for the trace amount of water present in the solid metal hydroxide and any small amount of water which may be present in the commercial 2-pyrrolidone. This is in sharp contrast to some prior art purification methods which add water to the commercial 2-pyrrolidone and/or use excessive amounts of additives containing substantial amounts of combined water.

Comparative Examples

The following experiments were carried out to compare ordinary vacuum distillation with treatment in a molecular still according to the present invention.

A. 300 g of commercial 2-pyrrolidone having a density at 30° C. of 1.1131 and a refractive index at 25° C. of 1.4587 were mixed with 1% (3g.) of analytical grade KOH. The mixture was divided into 2 parts of 151.5g. each.

1. One part was distilled from an ordinary distillation flask at 20 mm. pressure into a condenser using no fractionating column. The yield was 100 g (66%) of 2-pyrrolidone, $d^{30}$ 1.1127 and $n_D^{25}$ 1.4699. It began turning yellow after 1 day. When 100 g. was polymerized according to the method of U.S. Ser. No. 344,036, Filed Mar. 22, 1973, 51.3% of polymer having an inherent viscosity of 4.1 centipoises in formic acid at 25° C. was obtained.

2. The second part was distilled in the same apparatus at 0.5 mm pressure. The yield was 105 g. (69.31%) of 2-pyrrolidone, $d^{30}$ 1.1125 and $n_D^{25}$ 1.4702 which also began turning yellow upon standing. Polymerization of 100 g. in the same manner yielded 55.8% of a polymer having an inherent viscosity of 4.2 centipoises in formic acid at 25° C.

B. 300 g. of commercial 2-pyrrolidone was mixed with 1.5 g of analytical grade KOH and passed through a molecular still under the conditions described in Example 2. The yield was 282.9 g (94.3%) of 2-pyrrolidone, $n_D^{25}$ 1.4861, $d^{30}$ 1.1098. The reported figures are 1.4860 and 1.1110 respectively. The product was odorless and clear with no yellow color and remained colorless for over six-months. Polymerization of 100 g. in the same manner as in A (1) and (2) produced 95.9% of a polymer having an inherent viscosity of 10.3 centipoises in formic acid at 25° C. The polymerization procedure used above according to U.S. Ser. No. 344,036, filed Mar. 22, 1973, is as follows:

100 g. of purified 2-pyrrolidone (1.18 mole) are mixed with 5g. solid potassium hydroxide (0.09mole). The mixture is heated up slowly under vacuum in the presence of a nitrogen atmosphere. The temperature is raised to 107° C. under 2 mm. Hg and approximately 10% of the 2-pyrrolidone is distilled off to remove water formed during the reaction to form the 5-potassium salt of 2-pyrrolidone. The heating is discontinued and the solution is cooled down to room temperature. Next, bone dry carbon dioxide gas is bubbled through the solution in an amount sufficient to react with the potassium in the 2-pyrrolidone salt. After the $CO_2$ addition, the solution is poured into a bottle containing about 5% anhydrous potassium sulfate. The bottle is sealed and put into a constant temperature incubator for 48 hours at 48° to 52° C. The obtained polymer is ground into chips, washed to neutral pH and dried in an electrically heated oven (100°–105° C.).

The viscosity of the polymer was determined by the falling ball method on a ½% solution in 90% formic acid at 25° C.

The above comparative experiments demonstrate the unexpected superiority in purity of the 2-pyrrolidone purified by the method according to the present invention only by changing the apparatus in which the distillation is carried out to provide for non-equilibrium vacuum distillation. They also demonstrate the importance of the purity of 2pyrrolidone in obtaining a high yield of high viscosity (high molecular weight polymer.

The process according to the invention is commercially feasible and economical, since it is a simple, single distillation process requiring only one inexpensive reagent, the solid metal hydroxide.

The pure 2-pyrrolidone of the present invention is especially useful for those known uses of 2-pyrrolidone which benefit from the use of the pure, substantially anhydrous material. A particularly important use in this regard is the polymerization of this material to form polymers which can be extruded to form fibers of great utility.

Variations and modifications may be made within the scope of the claims and portions of the improvements may be used without others.

I claim:

1. A process for producing substantially pure, substantially anhydrous 2-pyrrolidone from impure liquid 2-pyrrolidone comprising the steps of:
   a. dissolving therein from about 0.1 to 0.8% by weight, based upon the weight of the impure 2-pyrrolidone, of a solid substantially anhydrous hydroxide of a metal selected from the group consisting of: sodium, potassium, lithium, barium and calcium;
   b. applying the hydroxide-pyrrolidone solution as a moving thin film to a heated surface under a vacuum pressure in a molecular distillation apparatus whereby the 2-pyrrolidone is selectively flash vaporized from the heated surface while the nonvolatile impurities of the solution remain on the heated surface;
   c. condensing the vaporized 2-pyrrolidone on a cooled surface; and
   d. collecting the condensed 2-pyrrolidone as substantially pure, substantially anhydrous, colorless and odorless 2-pyrrolidone, wherein the vacuum pressure and the distance between the heated surface and the cooled surface and their respective temperatures are selected so that no vapor-liquid equilibrium is formed and substantially all of the vaporized 2-pyrrolidone molecules move directly from the heated surface to the cooled surface without recondensing on the heated surface.

2. The process of claim 1 in which the impure liquid 2-pyrrolidone is first cooled below the melting point of 2-pyrrolidone to a temperature no lower than about 20° C. to cause solidification of the 2-pyrrolidone and separation of a small amount of liquid impurities, said liquid impurities are drained from the solid 2-pyrrolidone and the solid 2-pyrrolidone is warmed to a temperature no greater than about 28° C to cause it to liquefy for purification according to the process of claim 1.

3. The process of claim 1 in which the hydroxide of a metal is potassium hydroxide.

4. The process of claim 1 in which the temperature of the heated surface is from about 90° to about 120° C. and the vacuum pressure is from about 0 to about 5 mm Hg.

5. The process of claim 4 in which the temperature of the heated surface is about 110°–115° C. and the vacuum pressure is from $10^{-4}$ to 2 mm Hg.

6. The process of claim 5 in which the hydroxide is used in an amount equal to about 0.5% by weight based upon the weight of the impure 2-pyrrolidone.

7. The process of claim 1 in which the rate of addition of the solution to the heated surface is sufficiently fast to cause a small amount of 2-pyrrolidone to remain on the heated surface to function as a solvent for the impurities and for the metal hydroxide.

8. The process of claim 1 which is carried out in a molecular distillation apparatus comprising a central heated column which is heated internally to form the heated surface, and an outer condensation wall forming the cooled surface and which has a temperature below the condensation temperature of 2-pyrrolidone under the vacuum pressure of the system.

9. The process of claim 1 which is carried out in a molecular distillation apparatus comprising an outer heated wall which is heated externally to form the heated surface, and a central condensation column forming the cooled surface and which is cooled internally to a temperature below the condensation temperature of 2-pyrrolidone under the vacuum pressure of the system.

10. The process of claim 1 in which the metal hydroxide is potassium hydroxide taken in an amount of about 0.1 to 0.5% by weight and the vacuum pressure is about 0 to 0.1 mm.

* * * * *